United States Patent
Lin

(10) Patent No.: US 9,095,616 B2
(45) Date of Patent: Aug. 4, 2015

(54) CAGED PLATINUM NANOCLUSTERS FOR ANTICANCER CHEMOTHERAPEUTICS

(71) Applicant: NATIONAL HEALTH RESEARCH INSTITUTES, Miaoli County (TW)

(72) Inventor: Shu-Yi Lin, Miaoli County (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 65 days.

(21) Appl. No.: 14/182,532

(22) Filed: Feb. 18, 2014

(65) Prior Publication Data

US 2014/0234413 A1  Aug. 21, 2014

Related U.S. Application Data

(60) Provisional application No. 61/766,281, filed on Feb. 19, 2013.

(51) Int. Cl.
*A61K 33/24* (2006.01)
*A61K 47/34* (2006.01)
*A61K 9/51* (2006.01)
*A61K 47/48* (2006.01)

(52) U.S. Cl.
CPC .............. *A61K 47/34* (2013.01); *A61K 9/5146* (2013.01); *A61K 33/24* (2013.01); *A61K 47/48207* (2013.01); *A61K 47/48215* (2013.01); *A61K 47/48238* (2013.01); *A61K 47/48853* (2013.01)

(58) Field of Classification Search
None
See application file for complete search history.

(56) References Cited

PUBLICATIONS

Kapp et al., Bioconjugate Chem., 2010, 21(2), pp. 328-337.*
Huizhen Zhu, "Applciations of Polyamidoamine Dendrimers in Polymer Electrolyte Membrane Fuel Cells", Thesis, 2009, pp. 1-114.*
Gao et al., Chem. Eur. J., 2012, vol. 18, pp. 8423-8429.*
Dhar et al. (2008), "Targeted delivery of cisplatin to prostate cancer cells by aptamer functionalized Pt(IV) prodrug-PLGA—PEG nanoparticles", PNAS 105(45): 17356-17361.
Xue at al. (2011), "Anti-tumor efficacy of polymer—platinum(II) complex micelles fabricated from folate conjugated PEG-graft-, -poly (N-amino acidy)-aspartamide] and cis-dichlorodiammine platinum(II) in tumor-bearing mice.", Colloids and Surfaces B: Biointerfaces 85: 280-288.
Long et al. (2010), "The synthesis and characterization of platinum nanoparticles: a method of controlling the size and morphology", Nanotechnology 21: 035605.

(Continued)

*Primary Examiner* — Brian Gulledge
(74) *Attorney, Agent, or Firm* — Hsiu-Ming Saunders; Intellectual Property Connections Inc.

(57) ABSTRACT

A caged platinum nanocluster complex is disclosed. The complex comprises (a) an amine-terminated dendrimer; and (b) a platinum nanocluster comprising platinum oxides, the platinum nanocluster being confined inside of the amine-terminated dendrimer. The complex exhibits cytotoxicity to cancer cells. A double-caged platinum nanocluster complex is also disclosed, which comprises polyethylene glycol (PEG) coated on the surface of a dendrimer caged platinum nanocluster complex. The double-caged caged platinum nanocluster complex comprises pH-sensitive bonds on the surface thereof. Also disclosed are methods of preparing and using the same.

20 Claims, 6 Drawing Sheets

(56) References Cited

PUBLICATIONS

Ye et at (2004) "Synthesis, Characterization, and Surface Immobilization of Platinum and Palladium Nanoparticles Encapsulated within Amine-Terminated Poly(amidoamine) Dendrimers" Langmuir 20, 2915-2920.

Borodko et al. (2012), "From Single Pt Atoms to Pt Nanocrystals: Photoreduction of Pt2+ Inside of a PAMAM Dendrimer", The Journal of Physical Chemistry letters 3, 236-241.

Han et al. (2008). "Effect of particle size and surface structure ran adsorption of O and OH on platinum nanoparticles: A first-principles study", Phys. Rev. B 77(7) 075410.

* cited by examiner

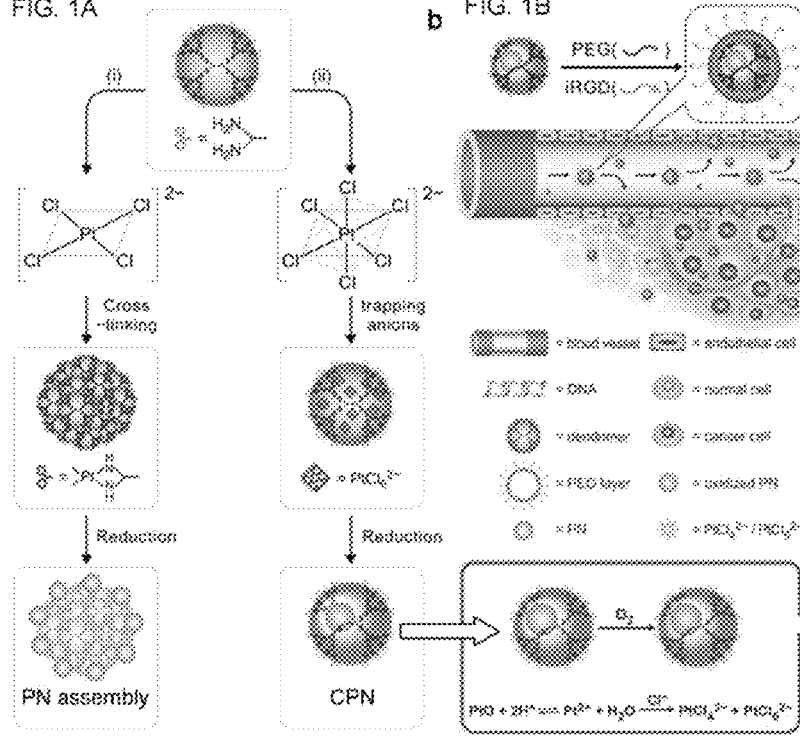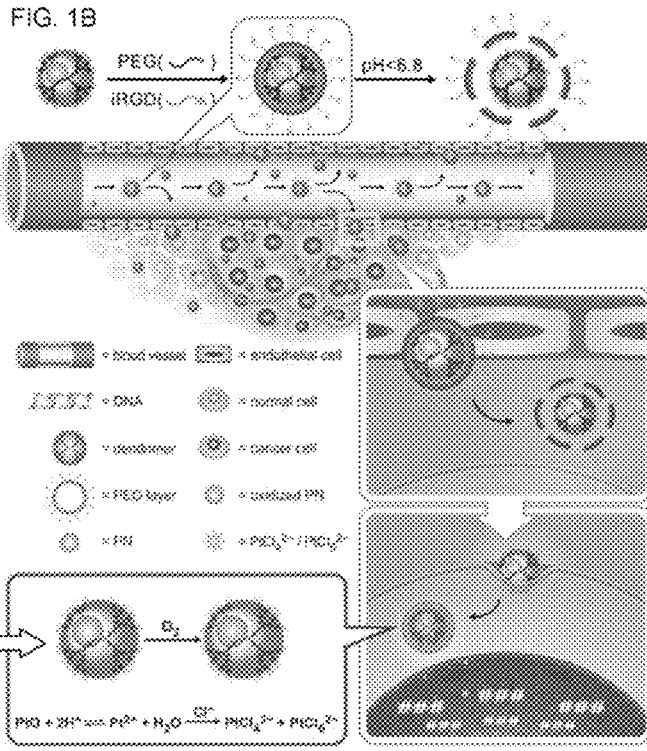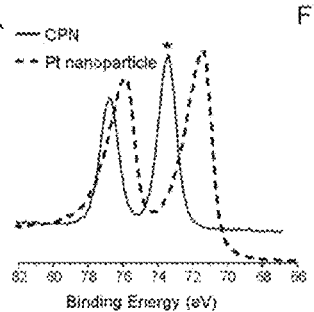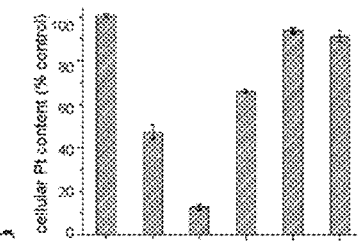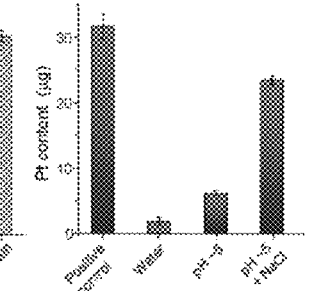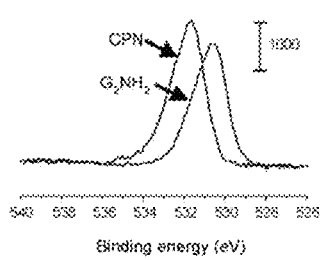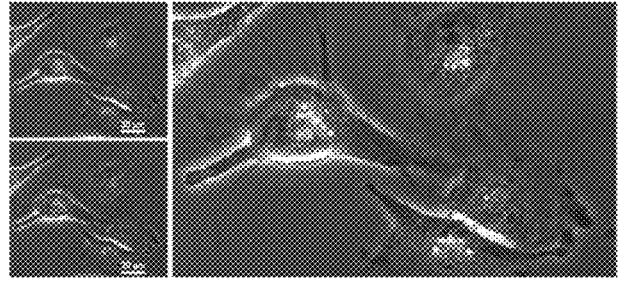

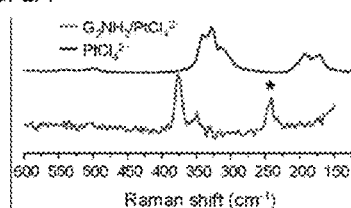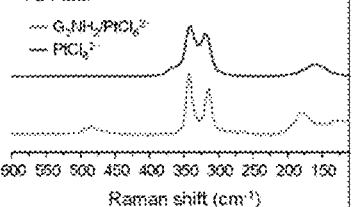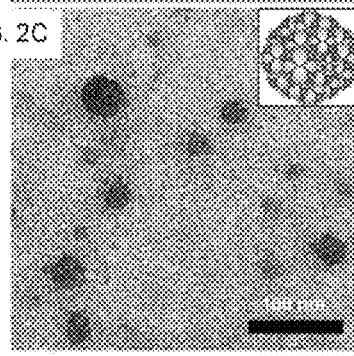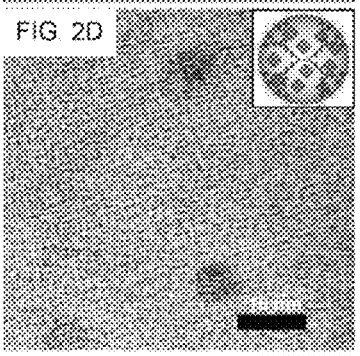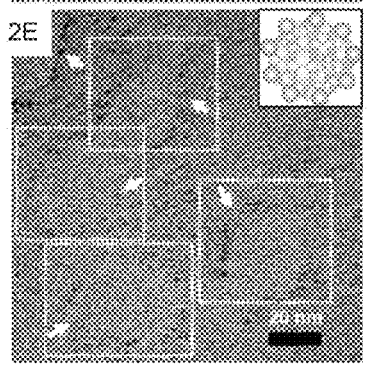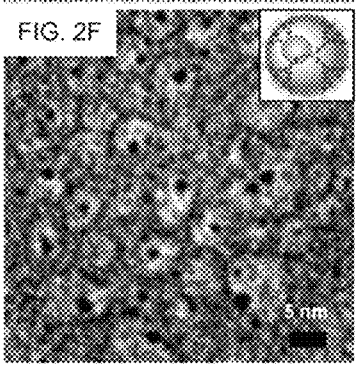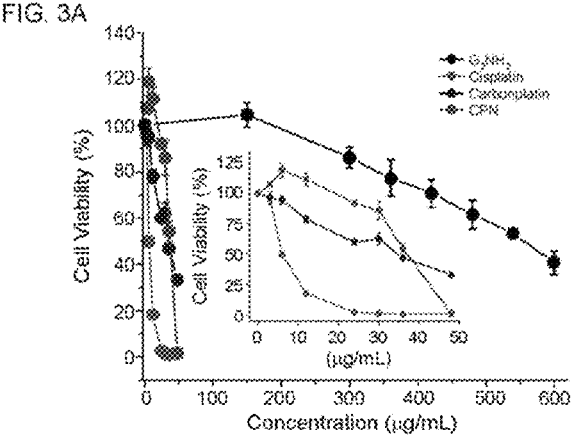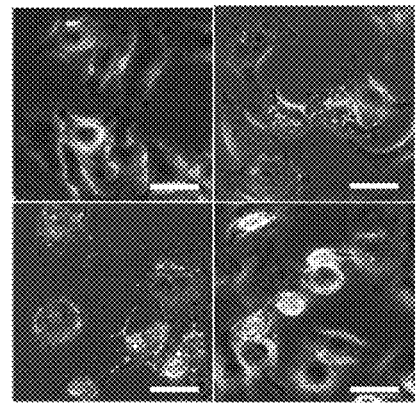

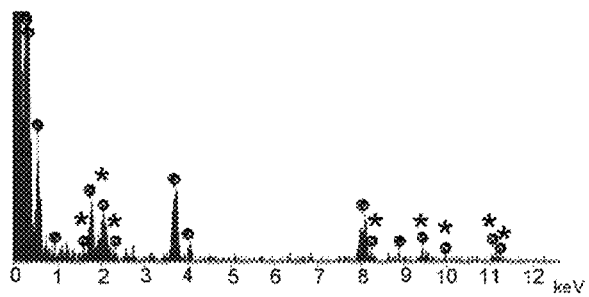
FIG. 6
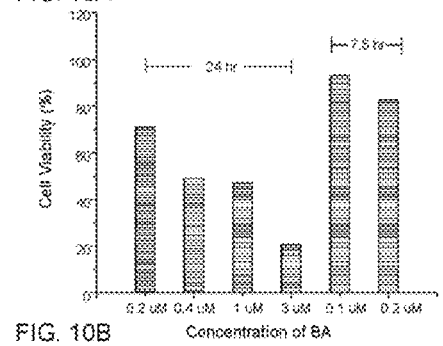
FIG. 10A
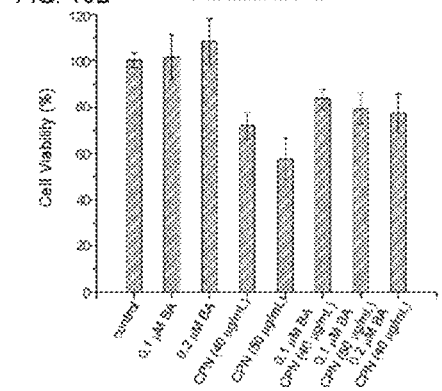
FIG. 10B
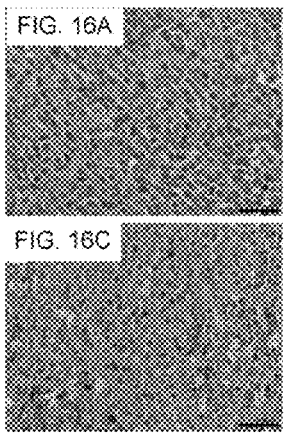
FIG. 16A
FIG. 16C
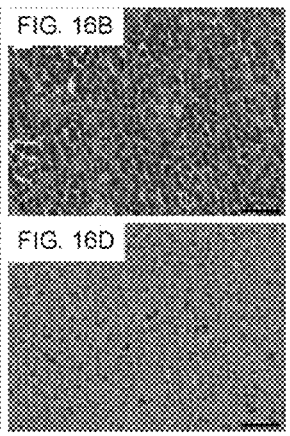
FIG. 16B
FIG. 16D
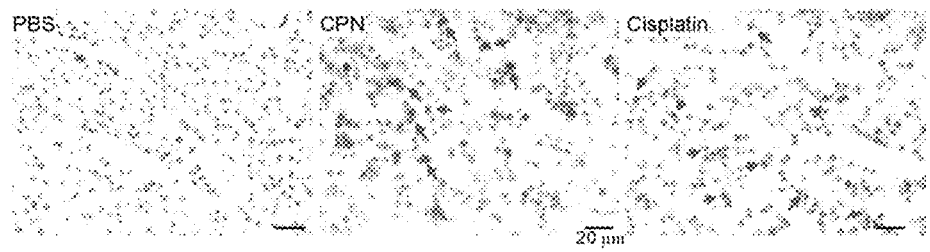
FIG. 11

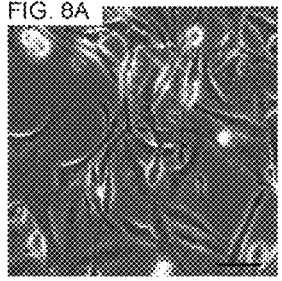
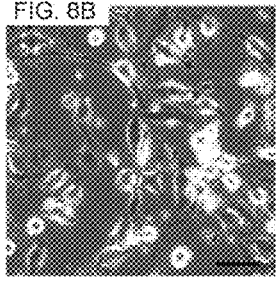
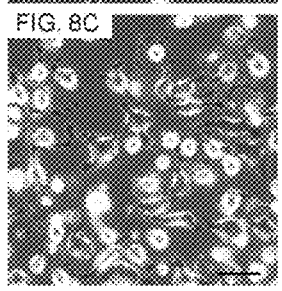
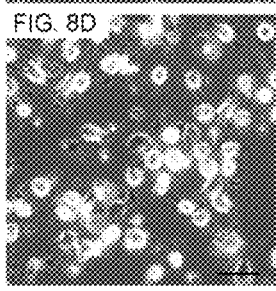
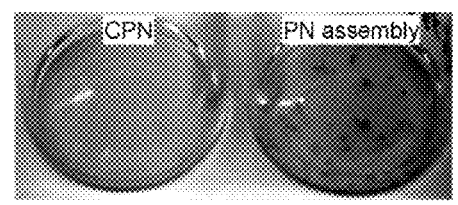
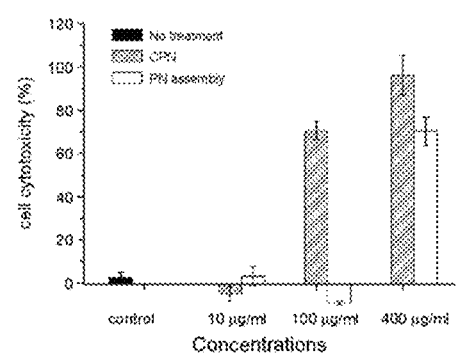
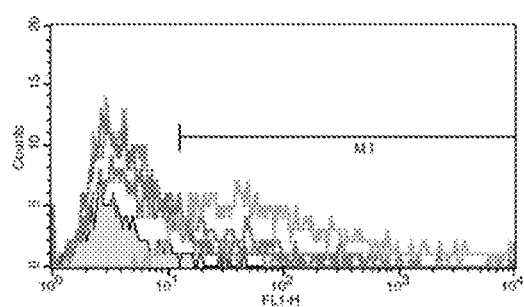
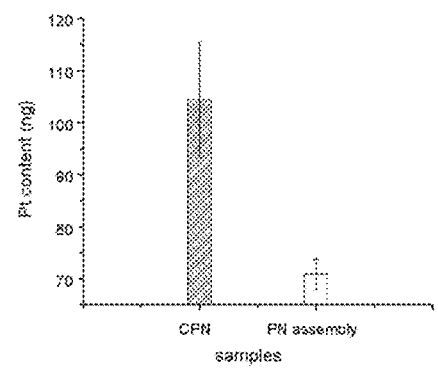

+ partial PEG cleavage ppm

CAGED PLATINUM NANOCLUSTERS FOR ANTICANCER CHEMOTHERAPEUTICS

REFERENCE TO RELATED APPLICATION

The present application claims the priority to U.S. Provisional Application Ser. No. 61/706,281, filed Feb. 19, 2013, which is herein incorporated by reference in its entirety.

FIELD Of THE INVENTION

The present invention relates to anticancer chemotherapeutics.

BACKGROUND OF THE INVENTION

Unlike the toxicity of cisplatin, which is activated simply by water. Pt is considered to be a noble metal that can only dissolve in highly corrosive agents such as aqua regia ($HNO_3$/HCl), which initially oxidizes and then dissolves Pt to form Pt chloride complexes. It has been recently discovered that the degree of oxidization can be increased significantly by decreasing the Pt size to increase the surface-to-volume ratio to allow oxygen adsorption and facilitate water oxidation for surface corrosion. However, finding a method to shrink Pt efficiently remains a challenge.

SUMMARY OF THE INVENTION

In one aspect, the invention relates to a double-caged platinum nanocluster complex, comprising: (a) a dendrimer; (b) a platinum nanocluster comprising platinum oxides, the platinum nanocluster being confined inside of the dendrimer; and (c) polyethylene glycol (PEG), coated on the surface of the dendrimer. The dendrimer may be an amine-terminated dendrimer.

In another aspect, the invention relates to a caged platinum nanocluster complex, comprising: (a) an amine-terminated dendrimer; and (b) a platinum nanocluster comprising platinum oxides and having an average diameter of 0.93 nm with a standard deviation of 0.22 nm, the platinum nanocluster being confined inside of the amine-terminated dendrimer.

Further in another aspect, the invention relates to a method for synthesizing a caged platinum nanocluster complex as aforementioned, comprising the steps of:
(a) admixing a first solution comprising octahedronal hexachloroplatinate anions with a second solution comprising an amine-terminated dendrimer or a hydroxyl-terminated dendrimer to form a mixture comprising a $PtCl_6^{2-}$ anion/dendrimer complex;
(b) incubating the mixture comprising the $PtCl_6^{2-}$ anion/dendrimer complex for a sufficient period;
(c) reducing the $PtCl_6^{2-}$ anion in the $PtCl_6^{2-}$ anion/dendrimer complex to form a mixture comprising a dendrimer caged platinum nanocluster complex;
(d) passing the mixture comprising the dendrimer caged platinum nanocluster complex through a filter to obtain a filtrate comprising the dendrimer caged platinum nanocluster complex; and
(e) freeze-drying the filtrate to obtain the dendrimer caged platinum nanocluster complex.

Further in another aspect, the invention relates to a method for synthesizing a double caged platinum nanocluster complex comprising:
(i) dissolving a dendrimer caged platinum nanocluster complex as aforementioned in a solvent to form a solution, the complex comprising:
  (a) an amine-terminated dendrimer or a hydroxyl-terminated dendrimer; and
  (b) a platinum nanocluster comprising platinum oxides, being confined inside of the amine-terminated or the hydroxyl-terminated dendrimer;
(ii) adding PEG-aldehyde into the solution provided that the dendrimer is amine-terminated or adding $PEG-NH_2$ into the solution provided that the dendrimer is hydroxyl-terminated; and
(iii) allowing the PEG-aldehyde to react with primary amines of the amine-terminated dendrimer, or allowing the $PEG-NH_2$ to react with the hydroxyl-terminated dendrimer, and thereby obtaining the double caged platinum nanocluster complex.

Further in another aspect, the invention relates to a method of suppressing tumor cell growth, comprising administering to a subject in need thereof an effective amount of the complex as aforementioned.

Yet in another aspect, the invention relates to a pharmaceutical composition comprising:
(a) a therapeutically effective amount of a complex as aforementioned; and
(b) a pharmaceutically acceptable carrier.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1A is a schematic representation of a novel strategy based on tuning anionic geometry for the formation of PN; paths (i) and (ii) show that the outward and inward of $G_2NH_2$ can associate selectively with square planar $PtCl_4^{2-}$ and octahedronal $PtCl_6^{2-}$, respectively.

FIG. 1B is a schematic representation of the caged PN mixed with a tumor-penetrating peptide to target the tumor and kill malignant cells by shedding, the outer PEG corona to exert tumor-inside activation. The key point of anticancer efficiency was based on the PN losing its intrinsic inertness (inset of red rectangle) to exhibit its dissolution in weakly acidic organelles.

FIGS. 2A-B show Raman spectra of the $PtCl_4^{2-}/G_2NH_2$ complex (A) and $PtCl_6^{2-}/G_2NH_2$ complex (B), showing the N—Pt—N coordination from the former complex.

FIGS. 2C-D show HRTEM images of the $PtCl_4^{2-}/G_2NH_2$ complex (C) and the $PtCl_6^{2-}/G_2NH_2$ complex (D) before reduction.

FIGS. 2E-F show that while the complex of (C) and (D) were reduced, the PN was caged in the $G_2NH_2$ exterior (E) and interior (F). All TEM samples were prepared fresh before two days of the measurement, and the as-prepared samples were naturally dried. All measurements were taken in the absence of negative staining.

FIG. 3A show that the $IC_{50}$ of CPN was higher than the $IC_{50}$ of both cisplatin and carboplatin. The magnified inset shows the lower concentration, ranging from 0 to 50 µg/mL.

FIG. 3B are microscope images for observing the pathway of cell death. MDA-MB-231 cells that were untreated or treated with CPN at approximately 50 μg/ml, for different times were double-stained with annexin V-FITC and PI. The upper panels from left to right show untreated cells and cells treated with CPN for 5 h. respectively. The lower panels show the cells treated with CPN for 10 h and 24 h, respectively. Scale bar: 30 μm.

FIGS. 4A-B are XPS spectra showing the binding energy of Pt (A) and oxygen (B), specially represented in (A) was the $Pt(4f_{7/2})$ and $Pt(4f_{5/2})$ region of the CPN and Pt nanoparticles. The asterisk indicates that the binding energy of the CPN had shifted to 73.4 eV. The binding energy was calibrated by the $Au\ 4f_{7/2}(83.7\ eV)$ peak of gold film deposited on the substrate as an internal standard.

FIG. 4C shows various endocytosis inhibitors used during cellular uptake to verify the internalization pathway of the CPN.

FIG. 4D shows confocal microscopy of the cellular uptake behavior of CPN on MDA-MB-231 cells; the CPN was labeled a FITC for visualization (green) and lysosomal tracker (red), and the co-localization of CPN and lysosomal tracker was yellow color. The cell morphology has changed due to the CPN toxicity.

FIG. 4E shows the dissolution of Pt from CPN of the invention to ionic form under an endosomal-mimicking environment as determined by ICP-MS. The CPN was dissolved in aqua regia (3:1 $HCl/HNO_3$) as a control.

FIG. 6 shows an EDS spectrum of the CPN. The asterisks represent Pt signals.

FIGS. 7A-C show comparisons of the properties of CPN and PN assembly. These materials were produced by tuning anionic geometry. A) Solubility representation. B) Cytotoxicity evaluation. C) intracellular uptake efficacy.

FIGS. 8A-D are microscopic images to compare cisplatin-induced cell death and CPN-induced cell death pathways. MDA-MB-231 cells that were untreated or treated with 30 μg/mL cisplatin for different times were double-stained with annexin V-FITC and PI. The upper panels from left to right show untreated cells (A) and cells treated (B) with cisplatin for 5 h, respectively. The lower panels show the cells treated with CPN for 10 h (C) and 24 h (D), respectively. Scar bar: 50 μm.

FIG. 9 shows the ROS production of the CPN. MDA-MB-231 cell line was cultured in RPMI 1640 medium (media were supplemented with 10% fetal bovine serum) under 5% $CO_2$ atmosphere at 37° C. The cells were inoculated with $1\times10^5$ cells per well in a 6-well cell-culture plate and cultivated at 37° C. for 24 h. Then, the culture medium was changed with the presence of various treatments, including $G_2NH_2$ alone, the CPN, cisplatin, and 0.03% $H_2O_2$ in the culture medium. The tests were performed for 3 h without changing the medium. After removal of the supernatant of cell culture medium, the cells were isolated for ROS assay using $CM-H_2DCFDA$ from INVITROGEN™.

FIG. 10A shows the estimated safe dosage and treatment time of BA. It is noteworthy that the BA is also well-known to easily cause MDA-MB-231 cell death, through impairing mitochondrial functions. Thus, the concentration of BA and treatment time should be minimized and shortened, respectively, avoiding cell death from the synergistic effect of inhibitor and CPN, resulting in no significant difference between the presence and absence of BA during the CPN treatment.

FIG. 10B shows endosomal/lysosomal pH-rising effects on the CPN cytotoxicity.

FIG. 11 shows apoptotic cell death induced by CPN observed by active caspase-3 immunostaining. Scale bar: 20 μm.

FIGS. 16A-D show comparative histological H&E staining in the excised tumors. Images A)-D), various treatments including PBS, $G_2NH_2$, DCPN, and cisplatin at 400× magnification.

DETAILED DESCRIPTION OF THE INVENTION

Figure 5:
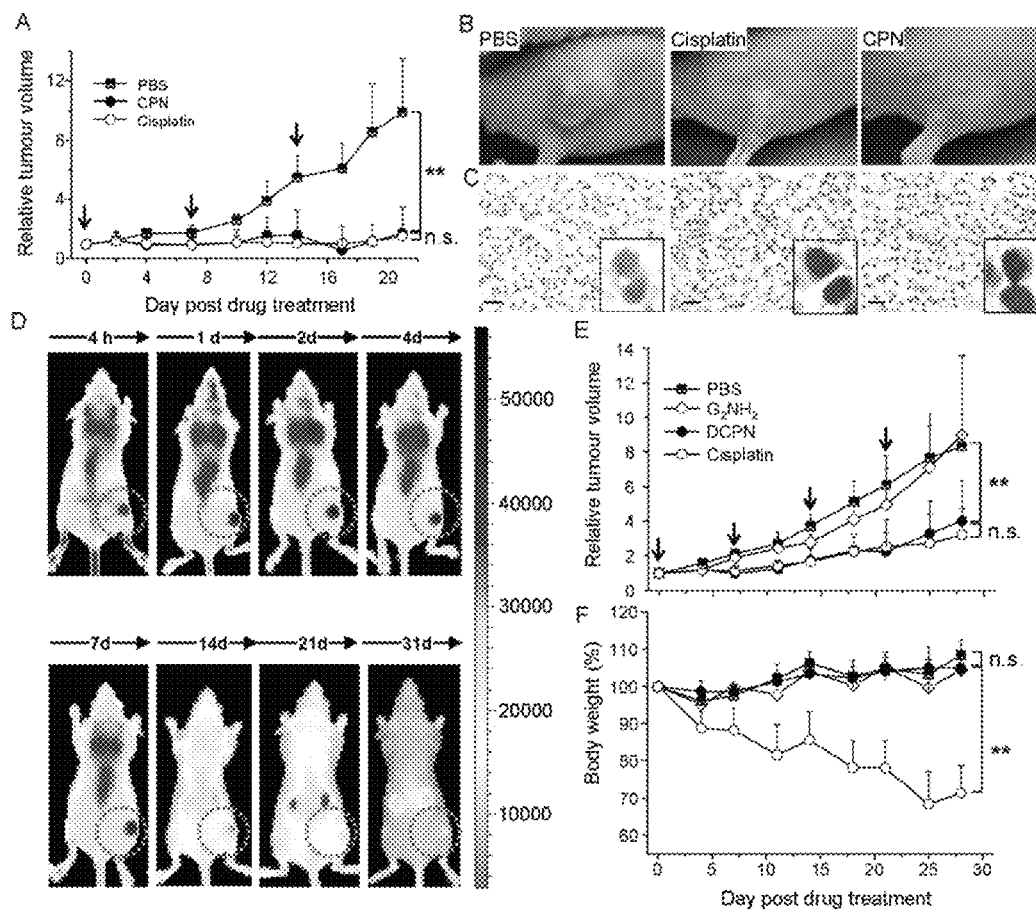
FIGS. 5A-F show anticancer therapeutic effects of CPN (A-C) and DCPN (D-F) evaluated after IT and IV injection, respectively. A) and E) Serial tumor volume, B) Representative images of tumor size at the end point for each group, C) the apoptotic cell death was observed using a TUNEL assay (scale bar: 20 μm), D) tumor target, and F) body weight were recorded. The sizes of nude mice bearing tumors were reached approximately 60 $mm^3$ and 150 $mm^3$ for IT and IV injection, respectively. The animal models were treated with two sets of treatments, which included IT injection (PBS, $G_2NH_2$, the CPN and cisplatin) and IV injection (PBS, $G_2NH_2$, iRGD, the DCPN and cisplatin). The profiles of $G_2NH_2$ in IT and iRGD alone in IV were omitted to avoid a complicated graph. The tumor volumes and body weight of mice were measured on the indicated days. Each data point represents the relative changes in mean tumor volume (n=5, P<0.05 and the n.s. indicated no statistical significance) after drug injection: error bars represent SD. Injection times are labeled by black arrows.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "nanocluster" refers to particles with diameters smaller than 2 nm or composed of less than 100 atoms.

Hexachloroplatinate anion has the chemical formula $[PtCl_6]^{2-}$.

Dendrimers are repetitively branched molecules. A dendrimer is typically symmetric around the core, and often adopts a spherical three-dimensional morphology. Dendrimers are also classified by generation, which refers to the number of repeated branching cycles that are performed during its synthesis. For example if a dendrimer is made by convergent synthesis, and the branching reactions are performed onto the core molecule three times, the resulting dendrimer is considered a third generation dendrimer. Each successive generation results in a dendrimer roughly twice the molecular weight of the previous generation. The first, the second, and the third generation dendrimers are designated as generation-1 (G-1), generation-2 (G-2) and generation-3 (G-3) dendrimers, respectively.

The term "caged" refers to being put or confined in or as if in a cage.

The term "a Schiff base" refers to an imine functional group. A Schiff base is formed from the condensation of an amine group with the carbonyl group of an aldehyde or ketone.

The term "dissolvability" refers to breaking up, being disintegrated or dissolved.

The terms "confined," "trapped," "caged", and "entrapped" are all interchangeable.

A filtrate is the fluid/liquid that has passed through the filter into the collection can after the filtration process.

End-group of dendrimer is also generally referred to as the "terminal group" or the "surface group" of the dendrimer. Dendrimers having amine end-groups are termed "amino-terminated dendrimers.

iRGD is a peptide (a chain of amino acids) that specifically recognizes and penetrates cancerous tumors but not normal tissues. The peptide was also shown to deliver diagnostic particles and medicines into the tumor. IRGD, could dramatically enhance both cancer detection and treatment. iRGD helps co-administered drugs penetrate deeply into tumor tissue. The peptide has been shown to substantially increase treatment efficacy against human breast, prostate and pancreatic cancers in mice, achieving the same therapeutic effect as a normal dose with one-third as much of the drug. MPEG (methoxy polyethylene glycol).

The term "treating" or "treatment" refers to administration of an effective amount of a therapeutic agent to a subject in need thereof with the purpose of cure, alleviate, relieve, remedy, ameliorate, or prevent the disease, the symptoms of it, or the predisposition towards it. Such a subject can be identified by a health care professional based on results from any suitable diagnostic method.

"An effective amount" refers to the amount of an active agent that is required to confer a therapeutic effect on the treated subject. Effective doses will vary, as recognized by those skilled in the art, depending on routes of administration, excipient usage, and the possibility of co-usage with other therapeutic treatment.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

$$HED = \text{animal dose in mg/kg} \times (\text{animal weight in kg/human weight in kg})^{0.33}.$$

HED may vary, depending on other factors such as the route of administration. For example for DCPN i.v. administration, if a mouse (20 gram BW) dose is 16.6 µmol/kg, then HED may be calculated as 16.6 µmol/kg×(0.02/patient's body weight)$^{0.33}$. For CPN IT injection, if a mouse dose is 7.5 mg/kg, then HED is 7.5 mg/kg×(0.02/patient's body weight).

Corrosive PN may be rapidly produced following a chemical reaction (FIG. 1, red rectangle) to allow the corrosive PN for subsequent dissolution. The dissolution rate can be accelerated by chloride ions. We hypothesized that intracellular acidic organelles (i.e., endosomes and lysosomes) possess proton sources and chloride ions to initiate the dissolution of the corrosive PN for DNA platination. However, finding a method to shrink Pt efficiently remains a challenge. We have developed a simple strategy based on the use of a low-generation and amine-terminated dendrimer ($G_2NH_2$) as a cage to trap a specifically geometric anion for the formation of caged PN (CPN. FIG. 1A). Given this corrodibility, the CPN was modified with an extra cleavable PEG corona and targetable molecules, such as iRGD, that can target tumors and release toxins against malignant cells by shedding the outer PEG corona to exert tumor-inside activation for anticancer chemotherapeutics (FIG. 1B) (Chien et al. "Caged Pt Nanoclusters Exhibiting Corrodibility to Exert Tumor-Inside Activation for Anticancer Chemotherapeutics" Advanced Materials, 2013, 25, 5067-5073, which is incorporated herein by reference in its entirety).

In one aspect, the invention relates to a double-caged platinum nanocluster complex, comprising: (a) a dendrimer; (b) a platinum nanocluster comprising platinum oxides, the platinum nanocluster being confined inside of the dendrimer; and (c) polyethylene glycol (PEG), coated on the surface of the dendrimer. The dendrimer may be an amine-terminated dendrimer In another aspect, the invention relates to a caged platinum nanocluster complex, comprising: (a) an amine-terminated dendrimer; and (b) a platinum nanocluster comprising platinum oxides and having an average diameter of 0.93 nm with a standard deviation of 0.22 nm, the platinum nanocluster being confined inside of the amine-terminated dendrimer.

In one embodiment of the invention, the platinum oxides are selected from the group consisting of PtO, PtOH, $PtO_2$, $Pt_xO_y$, and any combination thereof, wherein x, y are each independently an integer of larger than 0. The complex as aforementioned comprises no dendrimer aggregates and exhibits cytotoxicity to cancer cells.

In another embodiment of the invention, the PEG is conjugated to primary amines of the amine-terminated dendrimer through a Shiff base. The surface of the double-caged platinum nanocluster complex comprises pH responsive, or sensitive, bonds (such as double bonds). The pH responsive bonds exhibit disintegration and dissolution characteristics under an acidic condition, which affords a single caged platinum nanocluster complex (i.e., amine-terminated dendrimer caged platinum nanocluster complex, without PEG coating on the surface thereof).

In another embodiment of the invention, the double-caged platinum nanocluster complex exhibits an eye-shape appearance.

In another embodiment of the invention, the double-caged platinum nanocluster complex exhibits a characteristic of releasing $Pt^{2+}$, $PtCl_4^{2-}$ and/or $PtCl_6^{2-}$ ions under a condition with a pH less than 5.0. The platinum nanocluster exhibits dissolvability under a condition with a pH less than 5.0.

Further in another embodiment of the invention, the nanocluster has a diameter of less than 2 nm. Alternatively, the nanocluster has a spherical shape with a diameter of less than 3 nm.

Further in another embodiment of the invention, the dendrimer is a polyamidoamine (PAMAM) dendrimer. The complex as aforementioned may further comprise a tumor-penetrating peptide absorbed onto the surface of the dendrimer. The peptide may be iRGD (CRGDKGPDC: SEQ ID NO: 1).

Further in another embodiment of the invention, the dendrimer is selected from the group consisting of generation-0 (G-0), generation-1 (G-1), generation-2 (G-2), and generation-3 (G-3) dendrimers.

Further in another embodiment of the invention, the complex as aforementioned is free of hexachloroplatinate and/or tetrachloroplatinate anions.

Further in another embodiment of the invention, the surface or exterior of the amine-terminated dendrimer comprises no platinum nanocluster.

Further in another embodiment of the invention, the caged platinum nanocluster complex consists essentially of or consisting of:
  (a) an amine-terminated dendrimer; and
  (b) a platinum nanocluster, said platinum nanocluster comprising platinum oxides and being confined inside (interior) of the amine-terminated dendrimer.

In another aspect invention relates to a method of suppressing tumor cell growth, comprising administering to a subject in need thereof an effective amount of the complex as aforementioned. The tumor cell may be a breast cancer cell, or the subject may be afflicted with breast cancer.

Further in another aspect, the invention relates to a pharmaceutical composition comprising:
  (a) a therapeutically effective amount of a complex as aforementioned; and
  (b) a pharmaceutically acceptable carrier.

Further in another aspect, the invention relates to a method for synthesizing a caged platinum nanocluster complex as aforementioned, comprising the steps of
  (a) admixing a first solution comprising octahedronal hexachloroplatinate anions with a second solution comprising an amine-terminated dendrimer or a hydroxyl-terminated dendrimer to form a mixture comprising a $RtCl_6^{2-}$ anion/dendrimer complex;
  (b) incubating the mixture comprising the $PtCl_6^{2-}$ anion/dendrimer complex for a sufficient period;
  (c) reducing the $PtCl_6^{2-}$ anion in the $PtCl_6^{2-}$ anion/dendrimer complex to form a mixture comprising a dendrimer caged platinum nanocluster complex;
  (d) passing the mixture comprising the dendrimer caged platinum nanocluster complex through a filter to obtain a filtrate comprising the dendrimer caged platinum nanocluster complex; and
  (e) freeze-drying the filtrate to obtain the dendrimer caged platinum nanocluster complex.

Yet in another aspect, the invention relates to a method for synthesizing a double-caged platinum nanocluster complex, comprising the steps of:
  (i) dissolving a dendrimer caged platinum nanocluster complex as aforementioned in a solvent to form a solution, the complex comprising:
    (a) an amine-terminated dendrimer or a hydroxyl-terminated dendrimer; and
    (b) a platinum nanocluster comprising platinum oxides, being confined inside of the amine-terminated or the hydroxyl-terminated dendrimer;
  (ii) adding PEG-aldehyde into the solution provided that the complex comprises the amine-terminated dendrimer, or adding. $PEG-NH_2$ into the solution provided that the complex comprises the hydroxyl-terminated dendrimer; and
  (iii) allowing the PEG-aldehyde to react with primary amines of the amine-terminated dendrimer, or allowing $PEG-NH_2$ to react with the hydroxyl-terminated dendrimer, and thereby obtaining the double caged platinum nanocluster complex. The PEG may be MPEG.

The mixture recites in step (a), (b) or (c) is free of or does not comprise, silver ions, silver nitrate or $NaBH_4$.

The aforementioned method for synthesizing a complex may further comprise the step of purifying the dendrimer caged platinum nanocluster complex by removing excessive $PtCl_6^{2-}$ therefrom.

In one embodiment of the invention, the reducing step is performed by irradiation with microwaves.

In another embodiment of the invention, the incubating step is performed at room temperature overnight.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods:

Synthesis and Characterization of CPN.

$H_2PtCl_6$ (Acros, 200 μL, 30 μmol, 150 mM), and $K_2PtCl_4$ (UniRegion Bio-Tech, 200 μL, 30 μmol, 150 mm) were added to 20 mL of deionized water containing $G_2NH_2$ (Aldrich, 94.7 μL, 5 μmol, 20 wt % methanol solution), respectively. The mixture of $G_2NH_2$ and either $H_2PtCl_6$ or $K_2PtCl_4$ was incubated at room temperature overnight before being irradiated by microwave (CEM, Discover LabMate System, 300 W/120° C. and 30 min). After reduction, precipitated large platinum nanoparticles were filtered through a 0.22-μm membrane filter (Millipore, PES membrane, for platinum nanoclusters). The solution should be freeze-dried and then dissolved in ~1 mL water for further purification. To further remove extra anion ($PtCl_6^{2-}$ and $PtCl_4^{2-}$), anionic exchange chromatography (Merck, Fractogel EMD TMAE Hicap) was used to obtain purified CPN and PN aggregations. High-resolution transmission electron microscopy (HRTEM, JEOL-2010) was used to identify the size of the CPN and the PN assembly.

Synthesis of MPEG2000-Conjugated Benzaldehyde.

P-formylbenzoic acid (TCI, 10 equiv., 5 mmol, 751 mg) was dissolved in dichloromethane (20 mL) at room temperature, and DCC (Acros, N,N'-dicyclohexylcarbodiimide, 10 equiv., 5 mmol, 1 g), MPEG2000 (aldrich, 0.5 mmol, 1 g), and DMAP (Alfa. 4-Dimethylaminopyridine, 2.5 equiv., 1.25 mmol, 150 mg) were added sequentially. The reaction mixture was stirred for 24 h at room temperature. The sail was filtered off and the filtrate was concentrated, dissolved in isopropanol (20 mL), and cooled to 0° C. for 2 h. The resulting crystals were collected by filtration and washed with ethyl acetate. The crude product was dissolved in tetrahydrofuran and added to diethyl ether, dropwise. The precipitant was washed by diethyl ether twice. MPEG2000-benzaldehyde was recovered by evaporation under reduced pressure as a white powder. $^1$H NMR. (Varian, 400 MHz) of MPEG2000-benzaldehyde ($CDCl_3$): d 3.64 (proton of MPEG2000), 7.96 (d, 2H), 8.22 (d, 2H), 10.11 (aldehyde, s, 1H).

Synthesis of DCPN.

The CPN (5 µmol) was dissolved in DMSO (15 mL), and MPEG2000-benzaldehyde (40 µmol, 86 mg, prepared by the aforementioned step) or MPEG2000-$NH_2$ (40 µmol, 86 mg, commercially available) was added to the solution containing the CPN, caged by $G_2NH_2$ and $G_2OH$, respectively, at 37° C. for 4 h. Note that the CPN derived from $G_2OH$ and $G_2COOH$, the hydroxyl/carboxylate-terminated groups might be partially transformed to aldehyde-terminated groups for the reaction of MPEG2000-$NH_2$ via a Schiff base. Then, DMSO was removed, and the crude compound was purified by SEPHADEX™ G-10 column, using methanol as the eluent. The DCPN was recovered by evaporation under reduced pressure as blue powder. $^1$H NMR (Varian, 400 MHz) of the DCPN (d-DMSO): d 3.50 & 3.60 (protons of MPEG2000), 6.76 (d, br, 2H), 7.29 (d, br, 2H), 8.47 (imine, s, 1H).

Synthesis of DCPN with Labeling Cy5.5.

The CPN (5 µmol) was dissolved in DMSO 5 mL), and Cy5.5-NHS (GE healthcare), as a stock in DMSO (10 mg/mL, 5 µmol, 564 µL), was added. The reaction mixture was stirred at 37° C. for 16 h, then MPEG2000-benzaldehyde (40 µmol, 86 mg) was added to the solution for another 4 h under the same conditions. Then, DMSO was removed and the crude compound was purified by SEPHADEX™ G-10 column using methanol as the eluent. The DCPN was recovered by evaporation under reduced pressure as a blue powder. $^1$H NMR (Varian, 400 MHz) of the DCPN with labeling Cy5.5 (d-DMSO): d 3.38 & 3.49 (proton of MPEG2000), 6.66 (d, br, 2H), 7.23 (d, br, 2H), 8.49 (imine, s, 1H).

Cytotoxicity.

Cells of the MDA-MB-231 line (Bioresource Collection and Research Center, Taiwan) were cultured in RPMI 1640 medium supplemented with 10% fetal bovine serum under 5% $CO_2$ atmosphere at 37° C. Twenty-four-well cell culture plates were inoculated with $1 \times 10^5$ cells/well and kept at 37° C. for 24 h. The culture medium was changed in the presence of various concentrations of different treatments ($G_2NH_2$ alone, carboplatin, cisplatin, and CPN) in culture medium (three replicates). The tests were performed for 3 d without changing the medium. After the overlaying cell-culture medium was removed, the cells were incubated with 3-(4,5-dimethylthiazol-2-yl)-2,5-diphenyltetrazolium bromide (MTT, Sigma, Mo. USA) at 37° C. for 1 h. After treatment, the fomazan product from MTT was dissolved in DMSO and quantified using a conventional ELISA reader at 570 nm. For calibration, a blank test was performed in a 24-well plate under the same conditions.

To confirm the dissolution at in vitro level, the cell viability study of MDA-MB-231 cells was performed by co-treating with CPN and bafilomycin A1 (BA), a strong inhibitor of the vacuolar type H*-ATPase. Twenty-four-well cell culture plates were inoculated with $1 \times 10^4$ cells/well and kept at 37° C. for 24 h. BA is also well-known to easily cause MDA-MB-231 cell death through impairing mitochondrial functions. Thus, a low concentration of BA (≤0.2 µM) was adopted to gradually alter endosomal/lysosomal pH and shorten the treatment time to 6 hours. Cells were incubated with 0.1 µM or 0.2 µM BA and CPN (45 µg/mL) at 37° C. for 6 hours, followed by wash with PBS. WST1 reagent was added to each well (25 µL/well), and the mixture was reacted 2 hours before measurement.

Cell Apoptosis Assay.

An apoptosis kit (INVITROGEN™) was used to evaluate the number of cells undergoing apoptosis. For fluorescence microscopy, cells were cultured in medium containing SPNP for different times in 35-mm µ-Dish (ibidi) and apoptotic cells were then stained by fluorescence dyes using an annexin V-FITC/propidium iodide (PI) kit according to the manufacturer's instructions. The stained cells were observed under confocal microscopy (Olympus FV10i).

Analysis of Cellular Uptake Pathway:

MDA-MB-231 cells were placed into a six-well cell culture plate at $1 \times 10^5$ cells/well and cultivated at 37° C. for 24 h. The medium was replaced by a medium containing a specific endocytosis inhibitor (chlorpromazine 10 µg/mL or amiloride 1 mM or nystatin 25 µg/mL) and preincubated for 15 min. The medium was then removed, and medium containing the CPN and inhibitor was added. The control group received the CPN only. The medium was removed after 2 h, and the cells were washed with ice-cold PBS. After trypsinization, the cells were harvested, washed twice with ice-cold PBS, and centrifuged (2000 g, 4° C., 5 min) for storage at −20° C. until analysis. To determine the cellular platinum content, the cell pellet was homogenized in a Triton X-100 solution (1% w/w) and diluted for platinum analysis by inductively coupled plasma mass spectrometry (ICP-MS). The results were calculated as the average of three experiments.

The TUNEL Assay.

Terminal dexoxynucleotidyl trasferase-mediated dUTP nick end labeling (TUNEL) assay was used for in situ detection of apoptotic cell death. The frozen sections of tumor tissue (4 µm thick) were warmed up to room temperature. The slides were washed 3 times with PBS to remove OCT (one of tumor's embedded medium for frozen tissues). The labeling procedures followed the standard protocol of this kit. These slides were stained with 3,3'-diaminobenzidne (DAB, Thermo, S21024-2), then counterstained with hematoxylin and mounted onto glass coverslisps before monitoring by light microscopy.

Immunohistochemistry.

The frozen sections of tumor tissue (4 µm thick) were warm up to room temperature washed 3 times with PBS (5 min/time), and fixed with freshly prepared 4% paraformaldehyde in PBS for 15 minutes. The fixed sections were immersed in a polyclonal rabbit anti-mouse active caspase-3 antibody (Abcam Inc., ab2302, 5 µg/mL in 10% BSA of PBS, 50 µL/sample) at 4° C. for overnight, followed by washing with PBS (three times, 15 min/time) and incubating with peroxidase-conjugated polyclonal goat anti-rabbit antibodies (Abeam Inc., ab6721-200, 1:500 (v/v) in PBS, 100 µL/sample) at room temperature for 2 hours. These slides were first stained with DAB, subsequently counterstained with hematoxylin, and mounted with glass coverslisps before monitoring by light microscopy.

Animal Model and Tumor Suppression.

Seven-week-old female Balb/c nude mice (16-20 g) were kept on a 12-h light/12-h dark cycle at 24±2° C. and 50±10% relative humidity, with free access to water and food. They were subcutaneously injected with 2×10 cells/mouse to establish a breast tumor model. Tumors were measured by a digital Vernier caliper across each tumor's longest (a) and shortest (b) diameter, and tumor volume (V) was calculated by the formula $V=0.5a \times b^2$. When the tumor size reached approximately 60 mm$^3$ and 150 mm$^3$, CPN and DCPN were administered by IT and IV injection, respectively. The stud of comparative efficiency in tumor suppression was performed. The mice were treated with CPN via IT injections once a week for a total of 3 weeks. Similarity. DCPN was administered to mice via IV once a week for 4 weeks. The injection volume was 5 µL/g body weight and the tumor size was calculated every 2 to 3 days. After the mice were sacrificed, tumors and blood were collected and placed in EDTA glass tubes.

Results

We have used a low-generation, amine-terminated dendrimer ($G_2NH_2$) as a cage to trap a specifically geometric anion to form caged PN (CPN, FIG. 1A, path ii). The CPN was further modified with an extra cleavable PEG corona and targetable molecules, such as iRGD (CRGDKGPDC: SEQ ID NO: 1), which can target tumors and release toxins against malignant cells by shedding the outer PEG corona to exert tumor-inside activation for anticancer chemotherapeutics (FIG. 1B).

$G_2NH_2$ with low biosafety concerns was chosen as a cage to confine the PN size on an atomic level and provide endosomal uptake. However, the $G_2NH_2$, possessing a star-like structure and surrounding amine groups, presents challenges as a cage because it prefers to form large nanoparticles rather than small nanoclusters, and causes dendrimer aggregation through the coordination interaction between the peripheral amines and metal anions. To overcome these limitations, two anions with different geometries, square plane ($PtCl_4^{2-}$) and octahedron ($PtCl_6^{2-}$), were used, which can associate spontaneously with the $G_2NH_2$ exterior and interior, respectively. The $PtCl_4^{2-}$ can undergo a substitution reaction with the peripheral amines of $G_2NH_2$ easily. This nucleophilic displacement of $PtCl_4^{2-}$ can cause cross-linking with $G_2NH_2$, and therefore block the anion to enter the $G_2NH_2$ cavity (FIG. 1A, path i). After reduction, the surrounding Pt ions tend to form PN on the exterior of dendrimers through metallophilic attraction. In contrast, octahedron al anion ($PtCl_6^{2-}$) with steric hindrance slowly undergoes a substitution reaction to bind the peripheral amines, which can facilitate the interior trapping of $G_2NH_2$, through an electrostatic interaction between tertiary amines and $PtCl_6^{2-}$, and the subsequent PN formation (FIG. 1A, path ii).

Raman spectroscopy was used to verify which complex causes the substitution reaction. As shown in FIGS. 2A-B, a significant band appearing at 250 cm$^{-1}$ from the $PtCl_4^{2-}$/$G_2NH_2$ complex could be assigned to the N—Pt—N bending: vibration, indicating that the ligands of $PtCl_4^{2-}$ were labile to allow the replacement of peripheral amines of $G_2NH_2$. In contrast, no noticeable peak at 250 cm$^{-1}$ could be observed in the $PtCl_6^{2-}$/$G_2NH_2$ complex, suggesting that the steric effect of $PtCl_6^{2-}$ hindered the ligand replacement from $G_2NH_2$. Additionally, TEM measurements show direct evidence that verify the coordination differences in two complexes (i.e., $PtCl_4^{2-}$/$G_2NH_2$ and $PtCl_6^{2-}$/$G_2NH_2$). Apparently, the square planar anion ($PtCl_4^{2-}$) can be clearly seen to induce cross-linking of $G_2NH_2$ to form dendrimer aggregation with various diameters before reduction (FIG. 2C). Once the $PtCl_4^{2-}$/$G_2NH_2$ complex was reduced by microwaves, the PN was found to be produced and assembled alongside the surrounding of dendrimer aggregation (FIG. 2E, the white square and arrows). In contrast, only small nanoparticles (approximately 5 nm) in TEM image (FIG. 2D) were observed in the $PtCl_6^{2-}$/$G_2NH_2$ complex. This scale is somewhat larger than $G_2NH_2$-alone, implying that the repulsion force of anions causes the swelling of the $G_2NH_2$ cavity. Surprisingly, we found several eye-like nanoclusters in the TEM image (FIG. 2F), while the $PtCl_6^{2-}$/$G_2NH_2$ complex was reduced. Obviously, the PN was caged in a $G_2NH_2$ to form an eye-like structure with about 4 nm in diameter. Additionally, the internal nanocluster was estimated to be 0.93±0.22 nm in diameter. As a result, we concluded that the PN was caged in a $G_2NH_2$ as predicted in FIG. 1A (path ii). The CPN was measured by energy-dispersive x-ray spectroscopy (EDS) after removing extra anionic anions by using anionic exchange chromatography. FIG. 5 shows characteristic peaks from elemental Pt, which reconfirmed the presence of PN.

Their solubility in water was examined. The PN assembly around the dendrimer aggregation exhibited a poor water solubility compared to the CPN (FIG. 7A). Presumably, the peripheral amines were blocked by assembling the PN to decrease the solubility. FIG. 7B shows that the CPN had greater toxicity to cancer cells than the PN assembly, which might be correlated to the fact that the CPN has excellent solubility to maximize intracellular uptake of cancer cells. Cells treated with the CPN after 24 hours have a higher Pt accumulation than cells treated with the PN assembly (FIG. 7C).

A human breast-cancer cell line, MDA-MB-231, was used to investigate why the CPN was able to kill cancer cells. The IC$_{50}$ value of the CPN was about 37 µg/mL, which was higher than that of cisplatin (7 µg/mL) and somewhat higher than that of carboplatin (35 µg/mL) (FIG. 3A). MDA-MB-231 cells were treated with CPN and cisplatin respectively, and then double-stained with annexin V-FITC (a green dye for apoptosis) and propidium iodide (PI, a red dye for necrosis) to observe time-dependent apoptosis and necrosis (FIG. 3B). No significant fluorescence (left upper panel) was observed in the untreated control. Only green fluorescence (right upper panel) from annexin V-FITC was observed in the early stage of treatment, which indicated the induction of apoptosis in MDA-MB-231. cells after treatment with the CPN. Positive PI staining (lower panels) can be observed after a prolonged incubation period, indicative of an increase in dead cells. FIG. 8 shows a similar result from cisplatin-induced cell death. It indicated that the phenotype of CPN-induced cell death may be similar to that of cisplatin-treated cells, the mechanism of which is known to be DNA breakdown.

FIG. 9 shows that no significant ROS increase or decrease from the CPN and cisplatin, indicating that ROS production does not participate in cell death. Next, if the CPN was inert like bulk Pt, then no toxic ions can be dissolved. Thus, we speculated that our CPN with a size of approximately 1 nm had been oxidized to form the corrosive PN for further dissolution. To verify this possibility, we examined the degree of surface oxidation by x-ray photoelectron spectroscopy (XPS). FIG. 4A shows the main peak of Pt($4f_{7/2}$) appearing at 73.4 eV from the CPN, which is higher than that of the Pt nanoparticle (>1 nm, approximately 71.2 eV). The relatively high binding energy (i.e., 73.4 eV) has been suggested from Pt oxide, probably the PN might form PtO. XPS was also used to examine the O(1 s) spectrum for a rough estimation of the oxygen amount of the CPN. The binding energy of the O(1 s) peak appearing at 531.8 eV cannot be referred to values from previous studies because the CPN had been caged within dendrimers to alter the binding energy of O(1 s). However, there was a significant increase in the O(1 s) peak of CPN compared to that of $G_2NH_2$ alone (FIG. 4B), indicating that the CPN was oxidized. With this oxidization status, when our CPN is internalized into acidic organelles, the low pH and chloride ions may facilitate the dissolution of the CPN.

We examined the internalized pathway of the CPN by adjusting incubation temperatures and using various specific inhibitors. First, the MDA-MB-231 cells were treated with the CPN at 37° C. as a control (FIG. 4C. column 1). Second, the uptake of the CPN can be dramatically reduced to ~50% (column 2) and ~10 (column 3) while the treatment temperatures were post-chilled and pre-chilled to 4° C. respectively, indicating that energy-dependent pathways, such as the endosomal routes, were dominated. Finally, the cells were co-incubated with various inhibitors of endocytosis. Only chlorpromazine (column 4), an inhibitor for clathrin-mediated. endocytosis, can significantly suppress the CPN accumulation in cells compared to other inhibitors, such as amiloride (column 5) and nystatin (column 6). We concluded that the CPN can be taken inside the cell through a clathrin-dependent endocytosis, which was consistent with the internalized pathway of PAMAM dendrimer alone. We also found that the intracellular distribution of CPN can co-localize with a lysosomal tracker (FIG. 4D). This implied that CPN can enter these acidic endosomes/lysosomes for possible dissolution. To determine the quantity of Pt ions, the CPN was completely dissolved in aqua regia (3:1 $HCl/HNO_3$) as a positive control (FIG. 4E, column 1). The CPN was also treated with water (column 2), an acidic solution of pH 5 (column 3), and an acidic solution of pH~5 containing 80 mm NaCl (column 4). The amount of Pt ions was found to be significantly elevated in the acidic solution of pH~5 containing 80 mM. NaCl, indicating that the CPN possesses a pH-sensitive dissolution. To confirm the dissolution in vitro level, the MAD-MB-231 cells were co-treated with 0.1 μM or 0.2 μM bafilomycin A1 (BA, a strong inhibitor of the vacuolar type H'-ATPase) and CPN. The endosomal/lysosomal pH of MDA-MB-231 cells may be slightly increased after the BA treatment.; due to low tolerance of MDA-MB-231 cells in the presence of BA (the estimated safe dosage shown in FIG. 10A). FIG. 10B shows that CPN-induced cell deaths could be reversed significantly in a short time. This indicated that an acidification decrease of endosomes/lysosomes can impair Pt release. Taking the indication, the CPN may prevent premature interaction with the biological environment to minimize systemic toxicity.

Figure 12A:
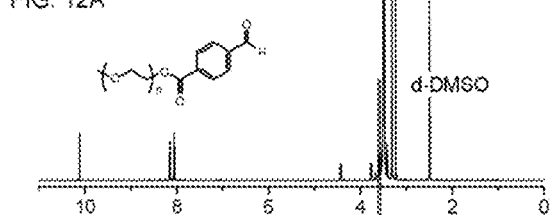
FIGS. 12A-C show $^3H$ NMR spectra from DCPN and its precursors.
Figure 12B:
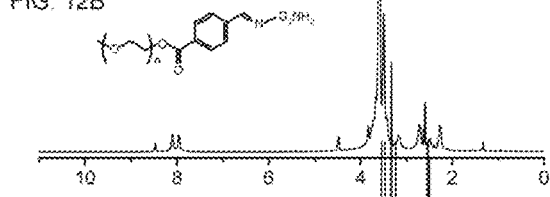
Figure 12C:
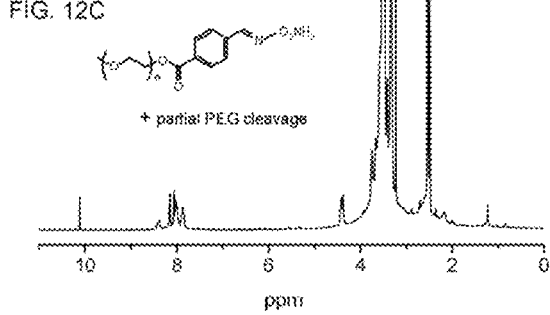
Figure 14:
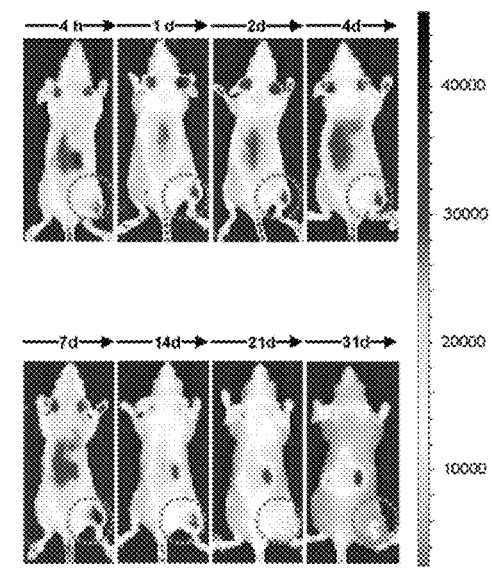
FIG. 14 shows comparative efficiency in tumor-targeting and anticancer chemotherapeutics of the $G_2NH_2$ coated with a cleavable PEG. No significant efficacy in tumor suppression was detected. The tumor mass at the end point is significantly larger than the one at the initial point.
Figure 13:
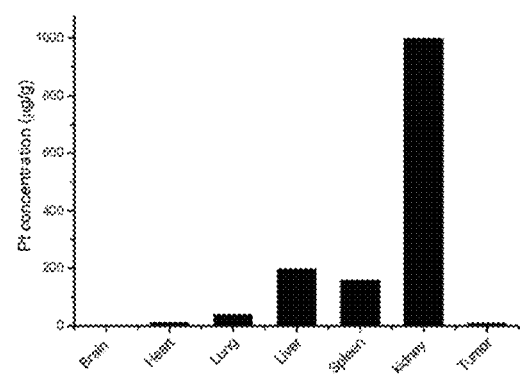
FIG. 13 shows bio-clearance of CPN after the end point.
Figure 15:
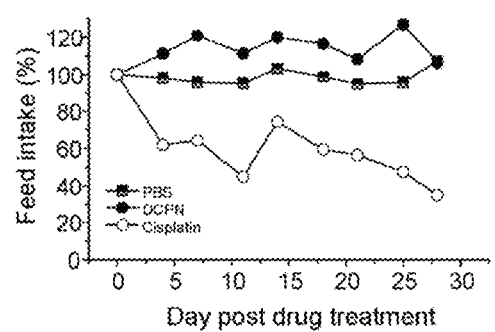
FIG. 15 shows feed intake of mice as recorded. Each data point represents the total amount of feed intake in each cage (n=5) after drug injection.

The therapeutic efficacy of CPN using subcutaneous breast cancer xenograft in mice was evaluated by intratumoral (IT) injection. The maximal tolerated dose (MTD) of various drugs, such as CPN and cisplatin, was described in Table 1. After IT injection, CPN and cisplatin were found to be notably efficacious in tumor suppression compared to two control groups (PBS and $G_2NH_2$) (FIGS. 5A-B). In addition, broken DNA strands can be detected by TUNEL assay (FIG. 5C), with brown nuclei (TUNEL-positive staining) being observed after treatment of CPN and cisplatin for 48 hours compared with blue nuclei (TUNEL-negative cells) of the control group. We also used immunohistochemical analysis to detect active caspase-3 to further confirm that the CPN-killing cancer cells can indeed cause apoptosis as well as cisplatin-killing cancer cells (FIG. 11). Thus, the programmed death pathway of CPN-treated cells might be similar to that of cisplatin-treated cells. We verified whether the CPN could be injected into blood vessels to exert tumor-inside activation for anticancer chemotherapeutics. Thus, the CPN was extra coated with a cleavable PEG layer to prevent protein adhesions after intravenous (i.v.) injection to form a double-caged PN (DCPN). The characteristics of DCPN are shown in FIG. 12, and the PEG corona was demonstrated to be cleaved from the DCPN in a tumor-mimic pH (pH 6.8). To render the DCPN with a targeting function, an iRGD tumor-penetrating peptide was co-administered with the DCPN into subcutaneous xenograft nude mice of breast cancer by IV administration. The tumor size in each mouse was grown to about 150 mm³ to facilitate DCPN delivery. Additionally, the DCPN and one of the control groups ($G_2NH_2$ coated with a PEG corona) were pre-attached with as NIR dye, cy5.5, for real-time tracking alter administration. For comparison, all groups, including PBS, $G_2NH_2$, the DCPN, and cisplatin were intravenously injected for 4 weeks under the co-administration of iRGD. FIG. 5D shows a significant cy5.5 signal in tumor after treatment, indicating the tumor targeting of the DCPN. The signal in tumor reached a plateau at 4 h and at day 1 after injection, revealing that the pegylation of CPN can facilitate long-blood, circulation to increase tumor uptake. The cy5.5 signal in liver and spleen is much weaker compared to that in lung and heart, indicating that the PEG mantle can also decrease the DCPN accumulation in liver. It is well-known that the lower generation dendrimers ($G_nNH_2$, n<5) can be easily eliminated by urinary excretion. Here, the signal in tumor and other organs can gradually decrease at day 14 and then concentrated in the kidney. At day 31, the signal in kidney can dramatically decrease, indicating that the DCPN can be excreted. FIG. 13 shows that the residual Pt in various organs (brain, heart, lung, liver, spleen, and kidney) was less than 15% (Table 2), indicative of the excretion of DCPN. Given the same dosage (16.6 μmol/kg) of all materials at 7-day intervals/week by IV injection, FIG. 5E shows that the DCPN and cisplatin can indeed cause tumors to shrink compared to the tumors of the two control groups (PBS and $G_2NH_2$)). The $G_2NH_2$ alone being coated with a cleavable PEG corona also exhibited significant tumor targeting (FIG. 14). Unlike the case of mice that were administered the DCPN, the tumor growth cannot be suppressed in the absence of PN. Moreover, we checked the adverse effects in mice that were given the DCPN and found no significant body weight loss (FIG. 5F) and no decrease in feed intake (FIG. 15), compared to those given cisplatin. Consecutive tissue sections front four groups, including the control, cisplatin, $G_2NH_2$, and DCPN groups were examined histologically by hematoxylin and eosin (H&E) staining at the end point, and the slides were evaluated by an independent pathologist (FIG. 16). The DCPN can also result m tumor cells necrosis after treatment, which was similar to the effect of cisplatin. Tables 1 and 2 show the dosage of Pt nanocluster used in n vivo experiments and estimated free Pt excretion of DCPN, respectively.

TABLE 1

| administration | Cisplatin[a] | CPN[b] | DCPN[c] |
|---|---|---|---|
| IT injection | 25 μmol/kg (7.5 mg/kg) | 14.4 μmol/kg (75 mg/kg) | X |
| IV injection | 16.6 μmol/kg | X | 16.6 μmol/kg |

[a]Molecule weight of cisplatin is 301.
[b]Molecule weight of the CPN = $G_2NH_2$ + 1 nm nanocluster (35 atoms Pt) = 3256 + 195 × 35 = 10,081
[c]Molecule weight of the DCPN = 8 (PEG 2 kD) + $G_2NH_2$ + 1 nm nanocluster (35 atoms Pt) = 8 × 2000 + 3256 + 195 × 35 = 26,081
**the amount of free Pt in the CPN = 14.4 μmol/kg × 35 atoms/1 nm Thus, the IT administered of free Pt is 504 μmol/kg.
**the amount of free Pt in the DCPN = 16.6 μmol/kg × 35 atoms/1 nm Thus, the IV administered of free Pt is 581 μmol/kg.

TABLE 2

| Organs | $A_1$ brain | $A_2$ heart | $A_3$ lung | $A_4$ spleen | $A_5$ kidney | $A_6$ Liver |
|---|---|---|---|---|---|---|
| Organ weight (g) | X | 0.172 | 0.249 | 0.125 | 0.592 | 2.093 |
| Pt amount (μg/g)$^a$ | ND | 11.55 | 39.34 | 156.4 | 996.9 | 195.1 |
| Total Pt amount in various organs (μg) | ND | 1.987 | 9.796 | 19.55 | 590.2 | 408.3 | accumulation in organs = $A_1 + A_2 + A_3 + A_4 + A_5 + A_6$ = 1029.8 (μg) = 1.0298 mg
∵ DCPN = 16.6 μmol/kg; 1 nm = 35 Pt atoms; Pt Mw = 195; mouse's weight ≈ 20 g
∴ Free Pt$^b$ = 16.6 μmol/kg × 35 = 581 μmol/kg
581 μmol/kg × 195 = 113.3 mg/kg
113.3 mg/kg × 0.02 kg = 2.27 mg
∵ injection times = 4 ∴ 2.27 mg × 4 = 9.06 mg
Thus, the residual Pt = (1.0298/9.06) × 100% = 11.4%
ND: not detect,
$^a$ the values were measured by ICP-Mass shown in FIG. 13.
$^b$ the free Pt within the CPN aid DCPN is identical, which was estimated in Table 1.

In summary, disclosed herein is a specially designed PN (i.e., the CPN), winch possesses tumor-inside activation for anticancer chemotherapeutics with minimizing systemic toxicity. By confining Pt's size to an atomic level (0.93±0.22 nm in diameter), it can be endowed with an attractive property for nanomedicine application as a prodrug. Specially, the PN can easily be oxidized, resulting in a loss of its intrinsic chemical inertness and a gain in surface corrodibility for further dissolution in weakly acidic organelles, such as endosomes and lysosomes, to release toxic Pt ions for DNA platination. The key point of this approach lies in controlling the size of the PN; thus, a novel synthesis strategy based on engine a specifically geometric anion into the $G_2NH_2$ interior has been developed. The feasibility of the CPN in exerting tumor-inside activation was confirmed in vivo by post-modifying a pH-clearable PEG corona and mixing with a tumor-homing peptide, resulting in a significant suppression in tumour growth. This CPN with a unique activation mechanism for killing cancer cells can potentially inspire further interest in nanomedicine research for the development of noble metals-based prodrugs.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A double-caged platinum nanocluster complex, comprising:
    (a) a dendrimer;
    (b) a platinum nanocluster comprising platinum oxides, the platinum nanocluster being confined inside of the dendrimer; and
    (c) polyethylene glycol (PEG), coated on the surface of the dendrimer.

2. The complex of claim 1, wherein the platinum oxides are selected from the group consisting of PtO, PtOH, $PtO_2$, $Pt_xO_y$, and any combination thereof, wherein x, y are each independently an integer of larger than 0.

3. The complex of claim 1, wherein the dendrimer is an amine-terminated dendrimer.

4. The complex of claim 1, wherein the PEG is conjugated to primary amines of the amine-terminated dendrimer through a Shiff base.

5. The complex of claim 1, wherein the surface of the complex comprises pH-responsive bonds.

6. The complex of claim 1, further comprising a tumor-penetrating peptide absorbed onto the surface of the dendrimer.

7. The complex of claim 1, wherein the complex exhibits a characteristic of releasing $Pt^{2+}$, $PtCl_4^{2-}$ and/or $PtCl_6^{2-}$ ions under a condition with a pH less than 5.0.

8. The complex of claim 1, wherein the platinum nanocluster exhibits dissolvability under a condition with a pH less than 5.0.

9. The complex of claim 1, wherein the nanocluster has an average size of less than 1.3 nm.

10. The complex of claim 1, wherein the dendrimer is selected from the group consisting of generation-0 (G-0), generation-1 (G-1), generation-2 (G-2), and generation-3 (G-3) dendrimers.

11. The complex of claim 1, wherein the dendrimer is a polyamidoamine (PAMAM) dendrimer.

12. The complex of claim 1, which is free of a hexachloroplatinate and/or a tetrachloroplatinate anion.

13. The complex of claim 1, wherein the complex exhibits cytotoxicity to cancer cells.

14. A method of suppressing tumor cell growth, comprising administering to a subject in need thereof an effective amount of the complex of claim 1.

15. A method for synthesizing the complex of claim 1, comprising the steps of:
 (a) admixing a first solution comprising octahedronal hexachloroplatinate anions with a second solution comprising an amine-terminated dendrimer or a hydroxyl-terminated dendrimer, to form a mixture comprising a $PtCl_6^{2-}$ anion/dendrimer complex:
 (b) incubating the mixture comprising the $PtCl_6^{2-}$ anion/dendrimer complex or a sufficient period;
 (c) reducing the $PtCl_6^{2-}$ anion in the $PtCl_6^{2-}$ anion/dendrimer complex to form a mixture comprising a dendrimer caged platinum nanocluster complex;
 (d) passing the mixture comprising the dendrimer caged platinum nanocluster complex through a filter to obtain a filtrate comprising the dendrimer caged platinum nanocluster complex;
 (e) freeze-drying the filtrate to obtain the dendrimer caged platinum nanocluster complex;
 (f) dissolving the dendrimer caged platinum nanocluster complex in a solvent to form a solution;
 (g) adding PEG-aldehyde into the solution provided that the dendrimer is amine-terminated, or adding $PEG-NH_2$ into the solution provided that the dendrimer is hydroxyl-terminated; and
 (h) allowing the PEG-aldehyde to react with primary attunes of the amine-terminated dendrimer, or allowing the $PEG-NH_2$ to react with the hydroxyl-terminated dendrimer, and thereby obtaining the double caged platinum nanocluster complex.

16. A caged platinum nanocluster complex, comprising:
 (a) an amine-terminated dendrimer; and
 (b) a platinum nanocluster comprising platinum oxides and having an average diameter of 0.93 nm with a standard deviation of 0.22 nm, the platinum nanocluster being confined inside of the amine-terminated dendrimer; wherein said complex, when administered to a subject, suppresses tumor cell growth.

17. A method for synthesizing the complex of claim 16, comprising the steps of:
 (a) admixing a first solution comprising octahedronal hexachloroplatinate anions with a second solution comprising an amine-terminated dendrimer to form a mixture comprising $PtCl_6^{2-}$ anion/dendrimer complex;
 (b) incubating the mixture comprising the $PtCl_6^{2-}$ anion/dendrimer complex for a sufficient period;
 (c) reducing the $PtCl_6^{2-}$ anion in the $PtCl_6^{2-}$ anion/dendrimer complex to form a mixture comprising a dendrimer caged platinum nanocluster complex;
 (d) passing the mixture comprising the dendrimer caged platinum nanocluster complex through a filter to obtain a filtrate comprising the dendrimer caged platinum nanocluster complex; and
 (e) freeze-drying the filtrate to obtain dendrimer caged platinum nanocluster complex.

18. The method of claim 17, wherein the reducing step is performed by irradiation with microwaves.

19. The method of claim 17, wherein the incubating step is performed at room temperature overnight.

20. The method of claim 17, wherein step (e) further comprises:
 purifying the dendrimer caged platinum nanocluster complex by removing extra $PtCl_6^{2-}$ therefrom.

\* \* \* \* \*

```
                        SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: peptide iRGD

<400> SEQUENCE: 1

Cys Arg Gly Asp Lys Gly Pro Asp Cys
1               5
```